(12) United States Patent
Katanaev

(10) Patent No.: US 8,119,354 B2
(45) Date of Patent: Feb. 21, 2012

(54) CELL-FREE ASSAY PRODUCT AND METHOD OF USE THEREOF FOR MEASURING ACTIVITY OF FRIZZLED RECEPTORS

(75) Inventor: Vladimir Katanaev, Constance (DE)

(73) Assignee: Universitaet Konstanz, Constance (DE)

( * ) Notice: Subject to any disclaimer, the term of this patent is extended or adjusted under 35 U.S.C. 154(b) by 0 days.

(21) Appl. No.: 12/682,282

(22) PCT Filed: Oct. 9, 2008

(86) PCT No.: PCT/EP2008/063541
§ 371 (c)(1),
(2), (4) Date: Jun. 3, 2010

(87) PCT Pub. No.: WO2009/047295
PCT Pub. Date: Apr. 16, 2009

(65) Prior Publication Data
US 2010/0261201 A1    Oct. 14, 2010

(30) Foreign Application Priority Data

Oct. 9, 2007   (EP) .................................... 07019715

(51) Int. Cl.
| | |
|---|---|
| *G01N 33/53* | (2006.01) |
| *C12P 1/00* | (2006.01) |
| *C12P 21/06* | (2006.01) |
| *C12N 1/20* | (2006.01) |
| *C12N 15/00* | (2006.01) |
| *C12N 15/74* | (2006.01) |
| *C07K 1/00* | (2006.01) |
| *C07K 14/00* | (2006.01) |
| *C07K 17/00* | (2006.01) |

(52) U.S. Cl. ....... 435/7.1; 435/41; 435/69.1; 435/252.3; 435/320.1; 435/471; 530/350

(58) Field of Classification Search .................. None
See application file for complete search history.

(56) References Cited

U.S. PATENT DOCUMENTS 6,485,972 B1 * 11/2002 McMahon et al. ............ 435/374
2007/0099263 A1 * 5/2007 Milligan et al. ............. 435/69.1

FOREIGN PATENT DOCUMENTS

WO    2005105850    11/2005

OTHER PUBLICATIONS

Ahumada, et al., "Signaling of rat frizzled-2 through phosphodiesterase and cyclic GMP", Science, 298:2006-10 (2002).
Borchert, et al., "High-content screening assay for activators of the Wnt/Fzd pathway in primary human cells", Assay and Drug Development Technologies, 3 (2):133-141 (2005).
Brennan and Brown, "Wnt proteins in mammary development and cancer", J. Mammary Gland Biology and Neoplasia, 9(2):119-131 (2004).
Das Gupta, et al., "Functional genomic analysis of the Wnt-wingless signaling pathway", Science 308:826 (2005).
Gazit, et al., "Human frizzled 1 interacts with transforming Wnts to transduce a TCF dependent transcriptional response", Oncogene, 18(44):5959-66 (1999).
Huang and Klein, "The Frizzled family: receptors for multiple signal transduction pathways", Genome Biology, 5(234):1-7 (2004).
Katanaev, et al., "Trimeric G \protein-dependent frizzled signaling in *Drosophila*" Cell, 120:111-22 (2005).
Le Garrec, et al., "Establishment and maintenance of planar epithelial cell polarity by asymmetric cadherin bridges: a computer model", Dev. Dynamics, 235:235-46 (2006).
Liu, et al., "G protein signaling from activated rat frizzled-1 to the beta-Catenin-Lef-Tcf pathway", Science, 292:1718-22 (2001).
Logan and Nusse, "The Wnt signaling pathway in development and disease", Annu. Rev. Cell Dev. Biol., 20:781-810 (2004).
Safholm, et al., "A formylated hexapeptide ligand mimics the ability of Wnt-5a to impair migration of human breast epithelial cells", J. Biol. Chem., 281(5):2740-9 (2006).
Willert, et al.,"Wnt proteins are lipid-modified and can act as stem cell growth factors", Nature, 423:448-452 (2003).
ISR and written opinion for PCT/ EP 2008/063541 mailed Feb. 12, 2009.
EXT. Europ Search Report and written opinion for EP 07 019 715 dated Jan. 11, 2008.
Response to Oct. 15, 2009 EPO Office Action filed Apr. 6, 2010.
Response to Oct. 27, 2010 second EPO Office Action filed Feb. 23, 2011.

* cited by examiner

*Primary Examiner* — Robert Landsman
(74) *Attorney, Agent, or Firm* — Pabst Patent Group LLP

(57) ABSTRACT

The present invention relates to cell free assays for measuring receptor activity, especially for measuring a constitutive or a non-constitutive activity of frizzled re-ceptors and uses thereof. The present invention further concerns a method for measuring a constitutive or non-constitutive activity of a frizzled receptor and a method for obtaining an active frizzled receptor ligand.

18 Claims, 7 Drawing Sheets

FIG 1
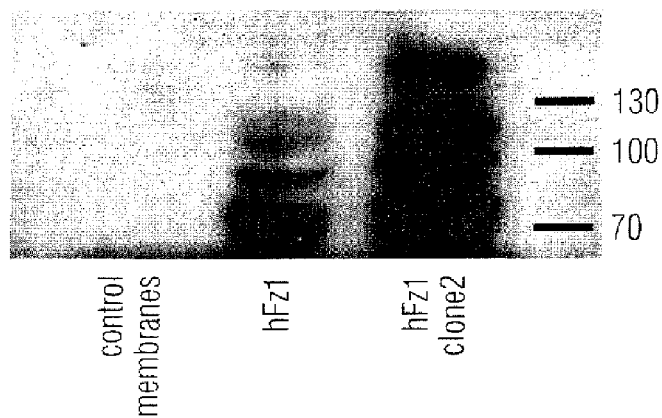
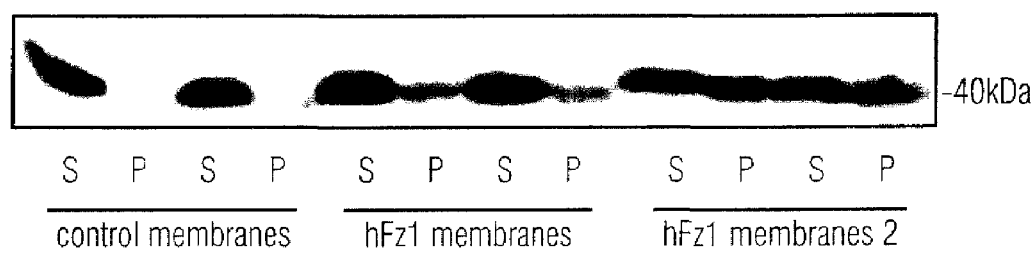

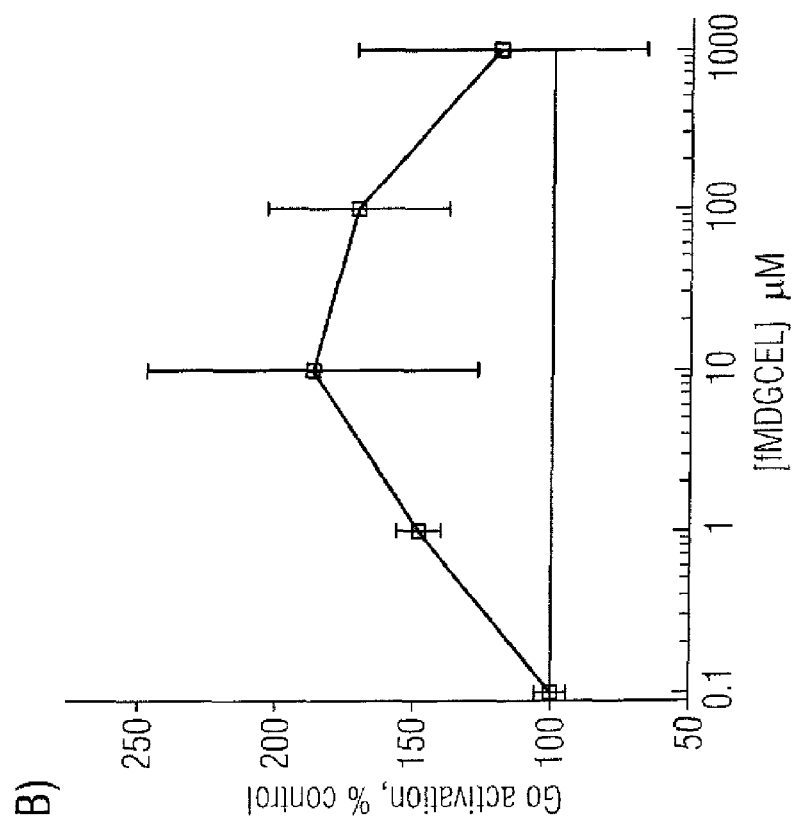
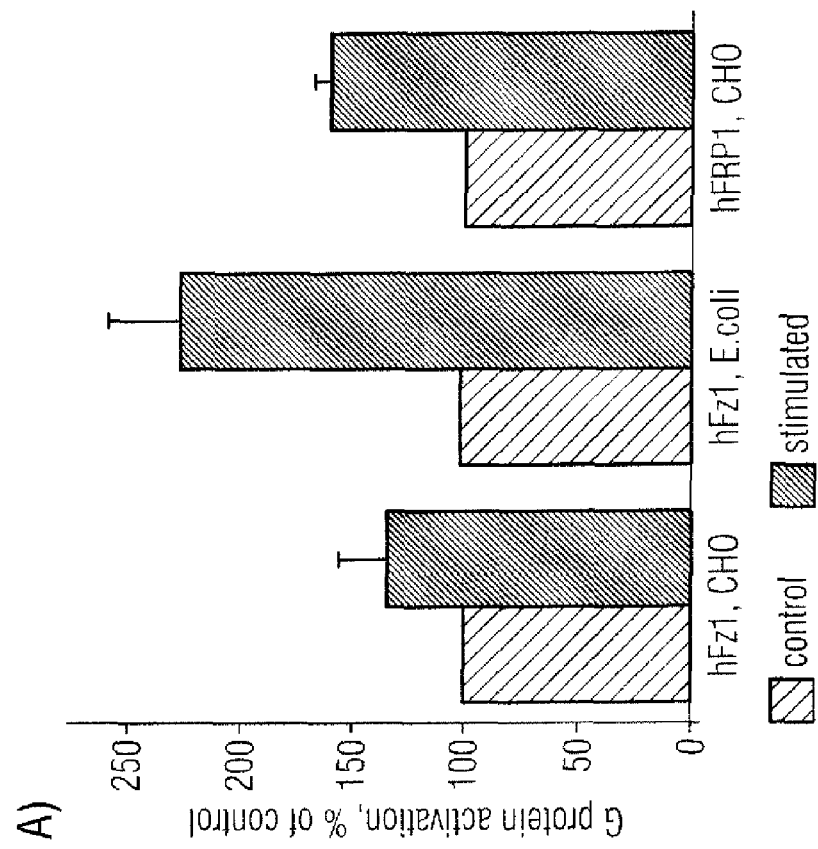
FIG 3

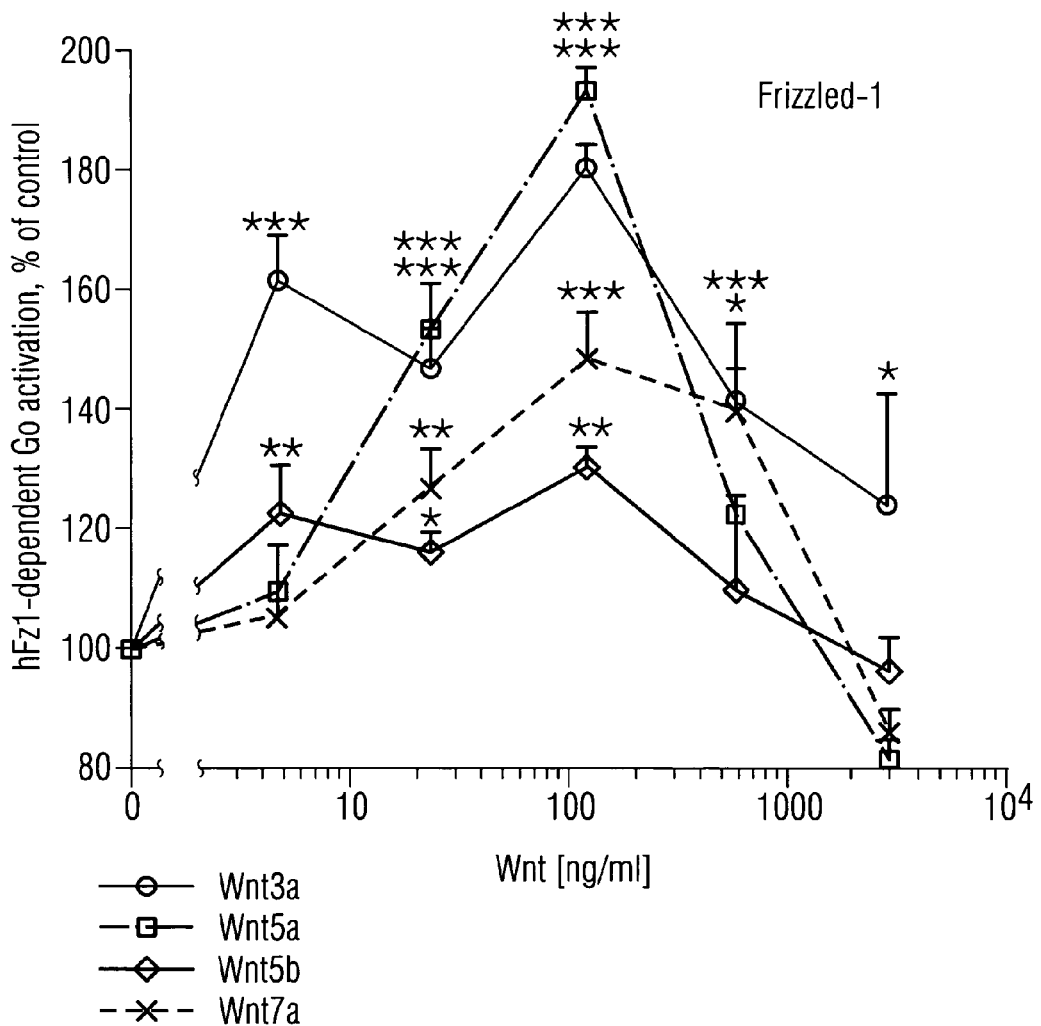

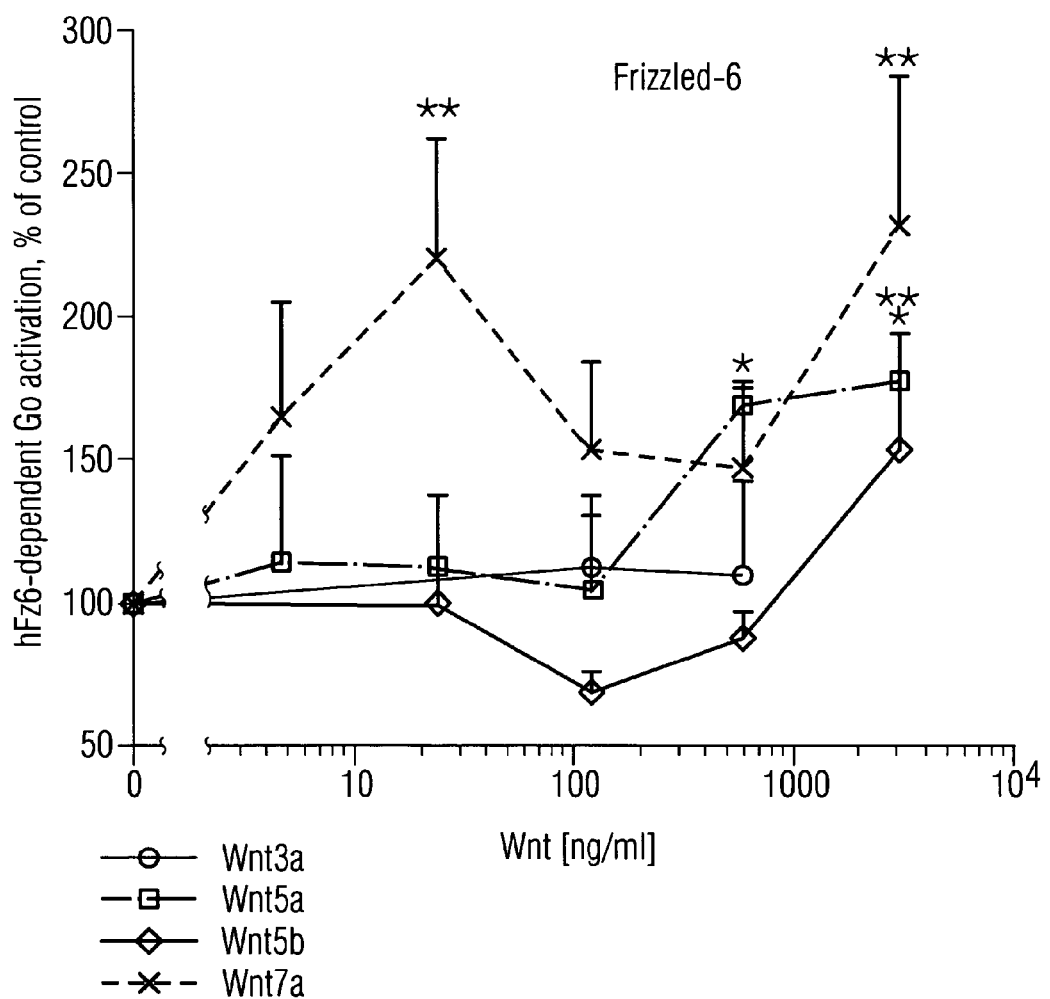

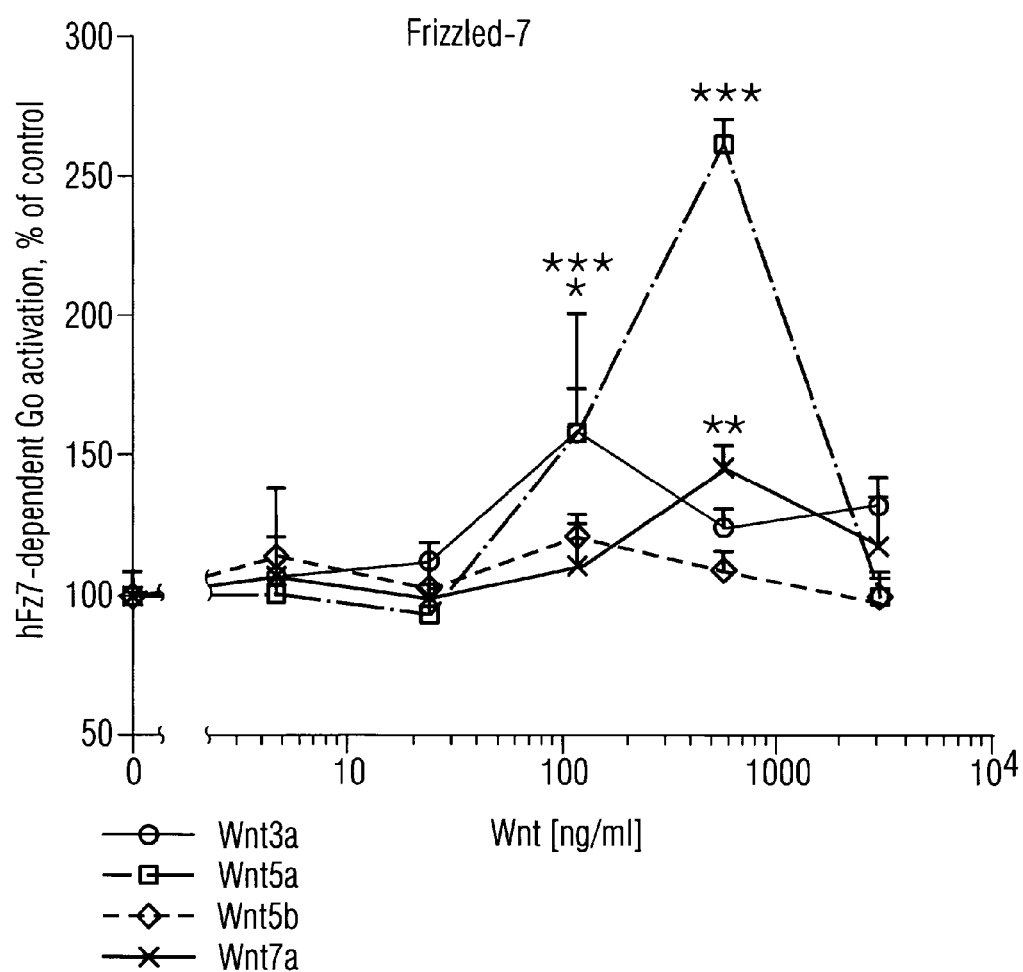

FIG 5 C

| Control | Wnt3a | Wnt5a | Wnt5b | Wnt7a |
|---------|-------|-------|-------|-------|
| hFZ1    | +++   | ++    | ++    | ++    |
| hFZ6    | -     | +     | +/-   | +++   |
| hFZ7    | +     | ++    | -     | +     |

CELL-FREE ASSAY PRODUCT AND METHOD OF USE THEREOF FOR MEASURING ACTIVITY OF FRIZZLED RECEPTORS

FIELD OF THE INVENTION

The present invention relates to the technical field of cell free assays for measuring receptor activity, especially for measuring a constitutive or non-constitutive activity of frizzled receptors. The present invention further concerns a method for measuring a constitutive or non-constitutive activity of a frizzled receptor and a method for obtaining an active frizzled receptor ligand.

BACKGROUND OF THE INVENTION

1. Cell Signaling

Cells use a large number of clearly defined signaling pathways to regulate their activity. These signaling pathways fall into two main groups depending on how they are activated. Most of them are activated by external stimuli and function to transfer information from the cell surface to internal effector systems. However, some of the signaling systems respond to information generated from within the cell, usually in the form of metabolic messengers. For all of these signaling pathways, information is conveyed either by protein-protein interactions or it is transmitted by diffusible elements usually referred to as second messengers or transmitters. The ability of cells to perceive and correctly respond to other cells is the basis of development, tissue repair, and immunity as well as normal tissue homeostasis. Errors in cellular information processing are responsible for diseases such as cancer, autoimmunity, and diabetes.

2. Wnt Proteins and Frizzled Receptors

Secreted Wnt (Wg Int) proteins have numerous signaling functions during development, mediated by certain receptors on the cell surface. These proteins are defined by their sequence rather than by functional properties. They contain a signal sequence of 350-380 amino acids followed by a highly conserved distribution of cysteines. Although Wnt proteins are secreted they show an insoluble nature that has been explained by the discovery that these proteins are palmitoylated and are more hydrophobic than initially predicted from the primary amino acid sequence. The palmitoylation is found on a conserved cysteine, suggesting that all Wnts essentially carry this modification (Willert K. et al., 2003). Until now this insoluble nature of all members of the Wnt family has hindered attempts to purify the Wnts and precluded an isolation of Wnts in high quantities.

Wnts proteins play diverse and essential roles in generation of cell polarity, embryonic induction, specification of cell fate, and diseases such as cancer or degeneration. At the molecular level, Wnt proteins operate largely via receptor-mediated signaling pathways, and these receptors appear to be members of the frizzled family (Huang H. and Klein P., 2004).

Frizzled receptors (Fz) are integral membrane proteins with transmembrane domains, an exposed binding site outside the cell and an effector site extending into the cytosol. They function in multiple signal transduction pathways and have been identified in numerous animals, from sponges to humans. The family is defined by conserved structural features, including seven hydrophobic transmembrane domains and a cysteine rich ligand-binding domain (Huang H. and Klein P., 2004).

Fz function in three distinct signaling pathways, known as the planar cell polarity pathway, the canonical Wnt/β-catenin pathway, and the Wnt/calcium pathway. The cytoplasmic Fz domains that link to heterotrimeric G proteins and other downstream signaling components transduce a signal to several intracellular proteins that include dishevelled, glycogen synthase kinase-3β (GSK-3β), axin, adenomatous polyposis coli (APC), and the transcriptional regulator β-catenin. Cytoplasmic β-catenin levels are normally kept low by continuous proteasome-mediated degradation, which is controlled by a complex containing GSK-3/APC/Axin. When cells receive Wnt signals, the degradation pathway is inhibited, and consequently β-catenin accumulates in the cytoplasm and nucleus. Nuclear β-catenin interacts with transcription factors such as lymphoid enhancer-binding factor 1/T cell-specific transcription factor to affect transcription. A large number of Wnt targets have been identified that include members of the Wnt signal transduction pathway itself, which provide feedback control during Wnt signaling (Logan C. and Nusse R., 2004).

Secreted proteins of the Wnt family play widespread roles in the regulation of embryonic development, and aberrant activation of the canonical Wnt/β-catenin pathway is one of the most frequent signaling abnormalities known in human cancer. In human breast cancer, evidence of β-catenin accumulation implies that the canonical Wnt signaling pathway is active in over 50% of carcinomas (Brennan K. and Brown M., 2004).

Much of last years' research focused on the development of cell based assays and screening techniques for drug discovery and design. Screening of cell signaling pathways in primary cells of a physiologically relevant phenotype provides a means to identify modulators of important disease pathways that lack known drug targets.

Borchert K. et al. (2006) screened for small molecule activators of Fz in primary human preosteoblasts that should contain intact and physiologically relevant Wnt/FZ signaling components. For this purpose they measured endogenous translocation of the downstream transcription factor β-catenin to the nucleus by combining standard immunofluorescent techniques with automated fluorescence microscopy.

DasGupta R. et al. (2005) used the availability of the *Drosophila* genome sequence, to find new components in the Wnt signaling pathway. By RNA interference (RNAi) based screening technology they identified functional genes regulating the Wnt-Wg pathway. The assay for the RNAi screen was based on the Wnt reporter TOP-Flash (TCF optimal promoter), which consists of multimerized TCF-binding sites driving the expression of a cDNA encoding the firefly luciferase gene. The screen was performed in *Drosophila* imaginal disc-derived clone 8 cells, which are epithelial in origin. The activity of the Wg signaling pathway was quantified by measurement of normalized luciferase expression or relative luciferase activity units, which equated to the ratio of the absolute activity of firefly luciferase to that of renilla luciferase.

Signal transduction has been studied extensively with cell based systems, but interest and commercial investment in Fz in areas such as drug targets, orphan receptors, high throughput screening, and biosensors, among others will focus greater attention on cell free assay development to allow for miniaturization, ultra-high throughput and, eventually, microarray/biochip assay formats. Although cell based assays are adequate for many Fz, these formats would limit the development of higher density Fz assay platforms mandatory for other applications. Stable, robust and cell free signaling assemblies comprising receptor and appropriate molecular switching components form the basis of future Fz assay platforms adaptable for such applications as microarrays. In addition cell free assays ensure a uniform response resulting in well-defined mechanisms of action and no ambiguity of experimental data due to other interfering and interactive pathways within the cell. Another advantage of cell free assays is the free accessibility of the compound to the target.

Thus there is a need for a fast and convenient cell free assay to measure the activity of Fz that is suitable for high throughput screening.

The solution to this problem is achieved by providing the embodiments characterized by the claims, and described further below.

SUMMARY OF THE INVENTION

It is an object of the present invention to provide a cell free assay for measuring a constitutive activity of frizzled receptors comprising at least one G protein, at least one system for measuring G protein activity and at least one membrane protein, wherein a concentration of the G protein is approximately 0.4 µg/ml or less, preferably between approximately 0.002 µg/ml and 0.3 µg/ml, more preferably between approximately 0.005 µg/ml and 0.15 µg/ml, most preferably approximately 0.1 µg/ml in relation to approximately 2 µg/ml to 15 µg/ml of the membrane protein.

Furthermore the invention concerns a cell free assay for measuring a non-constitutive activity of frizzled receptors comprising a G protein, at least one system for measuring G protein activity and at least one membrane protein, wherein a concentration of the G protein is approximately 0.3 µg/ml or higher, preferably between approximately 0.035 µg/ml and 10 µg/ml, more preferably approximately 0.4 µg/ml, most preferably approximately 0.5 µg/ml in relation to approximately 2 µg/ml to 15 µg/ml of the membrane protein.

In addition, the present invention is directed to a method for measuring a constitutive or non-constitutive activity of a frizzled receptor comprising the steps of:
a) providing at least one membrane protein with at least one cell free frizzled receptor;
b) adding at least one frizzled receptor ligand and at least one G protein; and
c) incubating the cell free frizzled receptor, the frizzled receptor ligand and the G protein in a system for measuring G protein activity, wherein the detection of guanosine triphosphate (GTP) binding to the G protein indicates the activity of the G protein.

The present invention is also directed to method for obtaining an active frizzled receptor ligand comprising the steps of:
a) performing random and/or directed mutagenesis in at least one polynucleotide sequence encoding at least one inactive frizzled receptor ligand to generate a mutated polynucleotide sequence;
b) digesting the mutated polynucleotide sequence into random polynucleotide fragments;
c) recombining the random polynucleotide fragments to obtain recombinant polynucleotides by at least one recombination technique;
d) cloning the recombinant polynucleotide into a vector;
e) expressing the recombinant polynucleotide resulting in recombined frizzled receptor ligands;
f) measuring the ability of the recombinant frizzled receptor ligands to activate frizzled receptors in a system comprising at least one G protein and at least one membrane protein with at least one frizzled receptor; and g) repeating step a) to f) until the recombinant frizzled receptor ligands activate the G protein at least 10-fold, preferably 100-fold, more preferably 500-fold, most preferably 1000-fold compared to frizzled receptor ligands encoded by the polynucleotide sequence of step a).

Furthermore the invention relates to the use of an assay for screening frizzled receptor ligands and/or for measuring levels of frizzled receptor ligands and/or for measuring levels of frizzled receptors and/or for obtaining active frizzled receptor ligands, wherein the assay comprises at least one G protein and at least one system for measuring G protein activity. A concentration of the G protein is approximately 0.4 µg/ml or less, preferably between approximately 0.002 and 0.3 µg/ml, more preferably between approximately 0.005 and 0.15 µg/ml, most preferably approximately 0.1 µg/ml in relation to approximately 2 to 15 µg/ml of membrane protein for measuring constitutive G protein activity, or is approximately 0.3 µg/ml or higher, preferably between approximately 0.035 and 10 µg/ml, more preferably approximately 0.4 µg/ml, most preferably approximately 0.5 µg/ml in relation to approximately 2 to 15 µg/ml of membrane protein for measuring non-constitutive G protein activity.

BRIEF DESCRIPTION OF THE DRAWINGS

FIG. 1(A) shows membrane fractions of control bacteria and two bacterial clones expressing a maltose binding protein (MBP) human Frizzled receptor 1 (hFz1) fusion protein (MBP-hFz1) in a western blot with anti-MBP.

FIG. 1(B) shows membrane fractions of control bacteria and two bacterial clones expressing hFz1 in a western blot with anti-Gαo.

FIG. 3(A) hFz1 membranes generated by CHO were activated by Wnt3a, E. coli-produced hFZ1 membranes were activated by purified Wnt3a, and for comparison, CHO membranes expressing human fMLP receptor hFRP1 were activated to a similar extent by a formyl-peptide ligand.

FIG. 3(B) produced hFz1 membranes generated by E. coli were stimulated with a Wnt5a-mimetic peptide.

FIG. 4 shows GTP incorporation into Go in the presence of different Wnt ligands. Incorporation is stimulated by detergent-solubilized hFz1.

FIGS. 5(A)-(C) show stimulation of several Frizzled receptors by Wnt ligands to activate the trimeric G proteins.

DETAILED DESCRIPTION OF THE INVENTION

Figure 2:
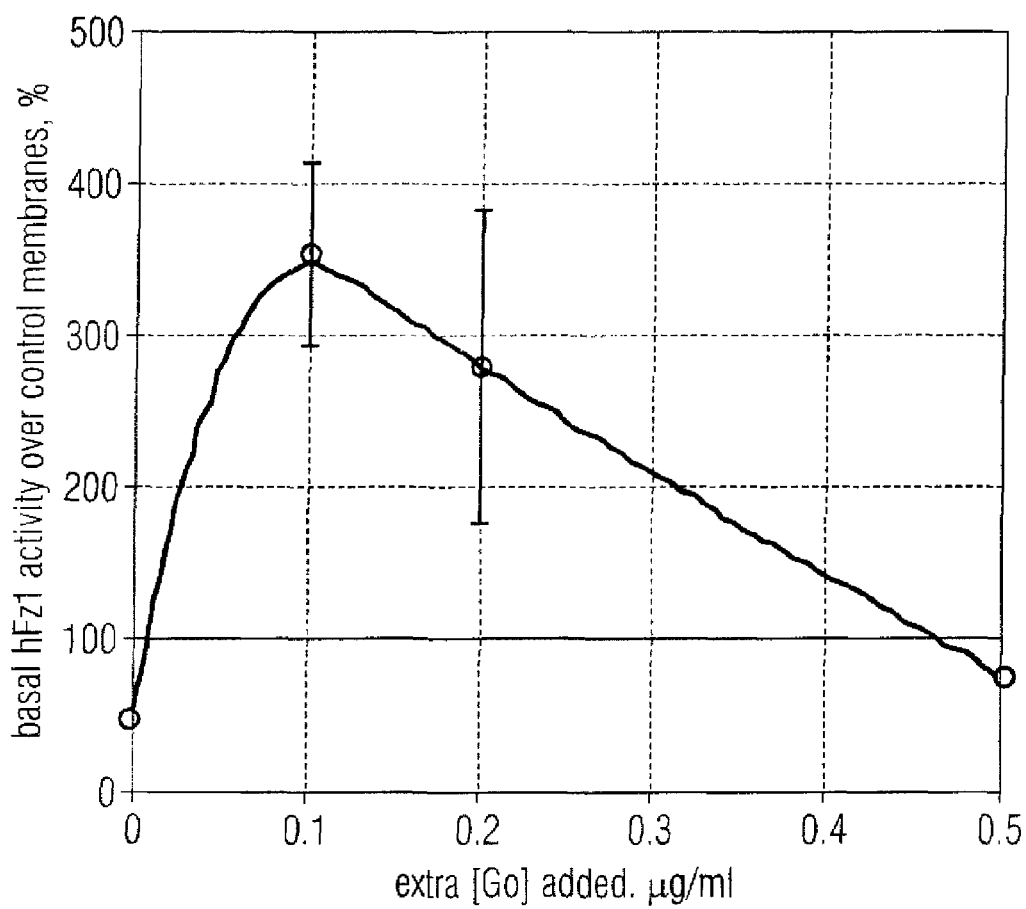
FIG. 2 shows the correlation of the constitutive G protein activity of hFz1 to the concentration of added G protein Go.

The present invention is directed to a cell free assay for measuring a constitutive activity of frizzled receptors comprising at least one G protein, at least one system for measuring G protein activity and at least one membrane protein, wherein a concentration of the G protein is approximately 0.4 µg/ml or less, preferably between approximately 0.002 µg/ml and 0.3 µg/ml, more preferably between approximately 0.005 µg/ml and 0.15 µg/ml, most preferably approximately 0.1 µg/ml in relation to approximately 2 µg/ml to 15 µg/ml of the membrane protein.

The term "cell free assay" as used herein refers to an assay, wherein no entire or intact cells are used. Cells can be disrupted by methods like enzymatic dissociation by lysozym; physical dissociation by ultrasound, French press, or glass-rod homogenizer; or non-isotonic buffers as hypotonic buffer with 10 mM Hepes etc. Disrupted cells exist as membrane fractions or cells with membranes perforated by antibiotics like gramicidine. The term "cell free" also means that receptors of the cell membranes can be coupled to a solid phase. Cell free assays are advantageous, because they are very robust and well suited for high throughput methods in micro formats. Their results are uniform and do not interfere with cellular interactions. Besides, cell free preparations provide a free accessibility to molecules of interest.

The term "constitutive activity" as used herein refers to a basal activity or intrinsic activity of receptors or proteins that does not depend on the presence of an exciting ligand or agonist of the receptor. Constitutive active receptors and proteins can spontaneously form active states that subsequently can activate downstream molecules like G proteins, thus producing a measurable response.

The term "frizzled receptors" as used herein refers to a family of heptahelicale serpentine receptors with integral membrane proteins comprising transmembrane domains, an exposed binding site outside the cell and an effector site extending into the cytosol. They range in length from about 500 to 700 amino acids forming a low density lipoprotein (LDL) receptor-related protein (LRP) complex at the cell surface. The amino terminus is predicted to be extracellular and contains a cysteine rich domain followed by a hydrophilic linker region of 40-100 amino acids. The proteins also contain seven hydrophobic domains that are predicted to form transmembrane helices. The intracellular carboxyterminal domain has a variable length and is not well conserved among different family members. A motif located two amino acids after the seventh hydrophobic domain is highly conserved in fz genes and is essential for activation of the Wnt/catenin pathway. Also comprised are frizzled-related proteins known as Frzb, that are homologous to Fz expressed e.g. in chondrocytes.

The fz genes were first identified in *Drosophila* and subsequently found in diverse metazoans, in vertebrates as fz1-10 and in *Caenorhabditis elegans*. Several fz genes appear to lack introns, however, including vertebrate orthologs of human fz1, fz2, and fz7 to fz10. Other fz genes, such as human fz5 and *Drosophila* frizzled2, contain one intron, but the entire open reading frame is encoded by a single exon.

Fz are found exclusively at the plasma membrane. They are located at the surface of Wnt-responsive cells, but may be internalized as part of a mechanism for regulating the extracellular level of Wnt protein and/or the cellular response to Wnt proteins.

Fz are typically coupled to trimeric G protein complexes. A G protein complex consists of a GDP bound α subunit and a βγ dimer and associates with intracellular portions of receptors. The term "activity of frizzled receptors" as used herein refers to activated receptors that catalyze exchange of GDP for GTP on Gα subunit. Dissociation of the complexes follows and the released Gα-GTP and βγ moieties are then free to engage with downstream effectors. By the time, the α subunit hydrolyzes GTP to GDP, generating the reformation of the complex and reassociation with the receptor.

Fz function in three distinct signaling pathways, known as the planar cell polarity (PCP) pathway, the canonical Wnt/β-catenin pathway, and the Wnt/calcium pathway as mentioned above. The PCP pathway is defined by the set of genes that, when mutated, result in defects in the polarity of cells in a planar tissue. Studies in mutant zebra fish and *Xenopus* suggest a role for Fz in oriented gastrulation movements in vertebrate, in which a convergent-extension phenotype arise through disruption of a PCP pathway. Asymmetric subcellular distribution of Fz has a central role in establishing cell polarity in flies and most likely in other organisms as well.

The canonical Wnt/β-catenin pathway is characterized by stabilization of β-catenin protein in response to ligand binding. β-catenin protein connects actin filaments to cadherins to build up adherent junctions between cells. Any excess of β-catenin is quickly destroyed by a multiprotein degradation complex that is partially encoded by tumor suppressor genes, e.g. APC tumor suppressor gene. In the absence of Wnt, GSK3 acts unopposed to phosphorylate both the scaffold axin as well as the β-catenin, which destabilizes β-catenin, directing it to degradation by the proteosome. In the presence of Wnt, Fz1 action inactivates GSK3β, stabilizes β-catenin, and leads to accumulation and translocation of β-catenin to the nucleus, where it combines with members of the Tcf family of DNA-binding proteins, enabling transcription. β-catenin has been shown to compete with the transcriptional repressor Groucho, transforming the transcription factor Tcf from a repressor to an activator (Huang H. and Klein P., 2004).

The term "G protein" as used herein refers to G proteins, short for guanine nucleotide binding proteins that are a family of proteins involved in second messenger cascades. They are called "G proteins" because of their signaling mechanisms, which use the exchange of guanosine diphosphate (GDP) for guanosine triphosphate (GTP) as a general molecular switch function to regulate cell processes. G proteins belong to the large group of GTPases. "G protein" usually refers to the membrane-associated heterotrimeric G proteins, sometimes referred to as the large G proteins. These proteins are activated by G protein-coupled receptors and are made up of alpha (α), beta (β) and gamma (γ) subunits. The definition for "G protein" used herein also includes small G proteins that belong to the Ras superfamily of small GTPases. These proteins are homologous to the α-subunit found in heterotrimers and are in fact monomeric. However, they also bind GTP and GDP and are involved in signal transduction. G proteins are perhaps the most important signal transducing molecules in cells. In fact, diseases such as cancer, diabetes, and certain forms of pituitary cancer, among many others, are thought to have some root in the malfunction of G proteins.

The term "G protein activity" as used herein refers to a G protein in an active state, wherein it is not bound to GDP. GDP bound G protein is inactive. Typically the inactive G protein is bound to its receptor. Once the ligand is recognized, the receptor, e.g. Fz, shifts its conformation and thus mechanically activates the G protein, which detaches from the Fz. In addition, the G protein activity can be a basal or constitutive activity that is spontaneous and not ligand gated. It is believed that G proteins and Fz exist in a conformational equilibrium between active and inactive biophysical states. The binding of ligands to Fz may shift the equilibrium toward the active Fz states. According to the definition used herein activated G proteins are bound to GTP disregarding whether G proteins are bound or not bound to the corresponding receptor. Also included are partially activated and desensitized G proteins. Activation of G protein catalyzes the exchange of GDP for GTP on Gα subunit, the G protein complex gets instable and tends to dissociate. By the released Gα-GTP and βγ moieties activated G proteins engage downstream effectors.

The term "system for measuring G protein activity" as used herein refers to a configuration, wherein the amount of active G protein is measured in a direct or indirect way. Therefore the amount of active or inactive G protein can be measured as well as transitions of an inactive to an active state and vice versa. The active or inactive state or the transitions between these states of downstream or upstream molecules of G proteins can also be quantified. In addition, the configuration can quantify the amount of bound and unbound ligands of G proteins; or the amount of down- or upstream molecules; or binding and release of these ligands. In a preferred embodiment the interaction between G protein and GDP or GTP, respectively, is detected. In the most preferred embodiment the GTP binding to G protein is detected by using labelled GTP.

The term "membrane protein" as used herein refers to all membrane proteins that are included in the phospholipid double or mono layer of cells, vesicles, compartments, membrane fragments, reconstituted detergent-containing or micelle-containing solutions or suspensions. Fz are a component of membrane proteins. Apart from Fz these membrane proteins may contain other membrane associated proteins. The quantitative portion of Fz in the overall amount of membrane proteins (Fz/total) depends on the design of expression system and experimental preparation of the membrane protein. The indicated values of the present invention concerning the concentration ratios of G protein to membrane protein are based on expression systems in bacteria and Chinese hamster ovary cells (CHO), and cell free preparations of membrane fractions as herein described in Materials and Methods, chapter 1 and 2. Other protein expression systems and membrane protein preparations may result in different Fz/total ratios. For example, in systems overexpressing Fz Fz/total is increased, whereas in systems with poor transfection efficiency Fz/total is decreased. Due to these possible variations of Fz/total the indicated values of the present invention concerning the concentration ratios of G protein to membrane protein have to be adjusted if expression and/or preparation conditions result in Fz/total that deviates compared to the Fz/total of the present invention. This adjustment has to put into effect that the ratio of G protein to Fz is according to the present invention. For instance, if the Fz/total of other systems is higher compared to the invention by e.g. Fz overexpression, the concentration ratio of G protein to membrane protein of the invention has to be increased, whereas if the Fz/total of other systems is lower compared to the invention by e.g. poor transfection efficiency, the ratio of G protein to membrane protein of the invention has to be decreased.

In a preferred embodiment of the invention membrane proteins are Fz. They can be provided in any kind of preparation e.g. in crude preparations, as extracts, purified, cell free as membrane fractions etc.

The present invention is based on the new and important finding that Fz are constitutively active receptors. As can be seen from FIG. 2, human frizzled receptors exemplified by hFz1 possess a strong constitutive activity towards trimeric G proteins. A very surprising effect was that this constitutive activity is restricted to a certain range of G protein concentrations. Typically one would expect that the higher the G protein concentration is the more constitutively active the Fz are until a saturated status with a constant activity is achieved. In contrast to this, higher G protein concentrations i.e. higher Go/Fz ratios led to an inhibition of the constitutive activity of G protein or Fz, respectively. This unexpected phenomenon is demonstrated by a bell shaped concentration dependent curve of the constitutive activity of hFz1.

Without intending to be bound by any theory it is believed that this concentration dependency of constitutive Fz activity can be explained by a negative feedback regulation. A constitutive active Fz activates Go, producing G$\alpha$o-GTP, and G$\alpha$o-GTP in turn inhibits Fz from generating more G$\alpha$o-GTP. Therefore, G$\alpha$o-GTP can inhibit its own production by inhibiting Fz to catalyze GDP/GTP exchange on the trimeric Go complexes. Thus, concentrations of G$\alpha$o-GTP and consequently constitutive G protein activity are well balanced.

Such a negative feedback interaction is unprecedented for receptors transducing via G proteins. Biologically, it might have the significance of ensuring a very transient activation of the intracellular signal transduction upon ligand addition to Fz. In fact, in the case of Fz controlled planar cell polarity signaling in *Drosophila*, mathematical modelling has predicted a very short time scale of Fz activation as a prime requirement for the proper planar cell polarity establishment (Le Garrec J. et al., 2006). This mathematical modelling is interpreted by a short-lived ligand that activates Fz. In contrary to this interpretation of Le Garrec J. et al., the data herein concerning the inhibition of constitutive activity with increasing G protein concentration suggest a negative feed-back in the Fz-Go interactions. Therefore, the Fz ligand does not have to be short-lived, but the intrinsic property of the Fz-Go interaction insures a short time period for active Fz by the negative feed-back.

On the basis of the constitutive activity of Fz or Fz coupled G proteins that is restricted to a certain range G protein concentration the present inventors developed a new assay for measuring the constitutive activity of Fz. In the assay of the invention the concentrations of G protein to Fz are provided in ratios, wherein the Fz or the Fz coupled G proteins are constitutively active. The assay makes use of this well defined restricted concentration range, wherein Fz or Fz coupled G proteins are specifically constitutively active. By experimentally presetting the concentration ratio of G protein/Fz to low values the assay defines the kind of Fz activity that can be modulated by adding ligands, modulators, effectors etc. Therefore, the present invention provides an assay for measuring specifically the constitutive activity of Fz.

By the assay of the present invention for measuring the constitutive Fz or G protein activity the influence of Fz ligands, e.g. Fz agonists, Fz antagonists, Fz modulators, Fz effectors etc., as well as all kind of modulators that are associated with the Fz pathway, e.g. effectors that bind apart from Fz e.g. to G proteins, inverse agonists, which switch off or reduce constitutive activity can be determined. It can be envisioned that e.g. an inverse agonist of the constitutive Fz activity will have an application as a drug reducing Fz activity in e.g. breast cancer or dementia. Therefore, this assay provides a high throughput screening technique to find pharmaceutical modulators of Fz activities in a simple, robust and fast manner.

The assay of the present invention for measuring the constitutive Fz or G protein activity is extremely useful for investigating Fz/ligand interactions and for screening Fz ligands. If optimal concentrations of Go for the constitutive hFz1 activity are used, Fz can not be activated further by ligand binding, but instead a 20%±10% reduction in Fz activity is produced upon binding of e.g. an agonists.

Another advantage of this assay of the present invention is its utilisation for orphan Fz, whose function and/or ligands are still unknown. Measuring the constitutive activity of these orphan receptors by the assay of the present invention is the only way to investigate the interaction of modulators, effector and ligands with Fz orphan receptors. Therefore the assay is ideal for discovering and screening unknown orphan receptor ligands producing a measurable response.

Another favorable property of the assay of the present invention for measuring the constitutive Fz or G protein activity is the fact that in vitro binding of Go to Fz as showed in FIG. 1 is not inhibited by addition of GTP or GTP$\gamma$S. These and other data of the present inventor reveal the unexpected property of the Go-Fz interactions, that these interactions persist even when the trimeric Go complex is dissociated into the GTP-loaded G$\alpha$o subunit and the beta-gamma heterodimer. Such persistence is undisclosed so far in the prior art and is believed to be not the case for the majority of other GPCRs and their cognate G proteins. Therefore, the measurements by the assay of the present invention concerning the constitutive Fz or G protein activity are not distorted by varying GTP concentrations.

The present invention is also directed to a cell free assay for measuring a non-constitutive activity of frizzled receptors comprising a G protein, at least one system for measuring G protein activity and at least one membrane protein, wherein a concentration of the G protein is approximately 0.3 µg/ml or higher, preferably between approximately 0.035 µg/ml and 10 µg/ml, more preferably approximately 0.4 µg/ml, most preferably approximately 0.5 µg/ml in relation to approximately 2 µg/ml to 15 µg/ml of the membrane protein.

The term "non-constitutive activity" as used herein refers to an activity of a receptor or protein that is dependent on the presence of an exciting ligand or an agonist that binds to the receptor causing a conformational change that is transmitted for activating downstream molecules. The non-constitutive activity is also called transmitter induced activity.

The present invention is based on the finding that Fz can be activated in a non-constitutively way. As can be seen from FIG. 3, Wnt3a and a Wnt5a-mimetic peptide can stimulate the Fz activity towards Go to a similar extent as an unrelated known GPCR can stimulate G protein activation. These findings are the basis for the assay of the present invention to screen for Fz ligands by measuring the non-constitutive activity of Fz.

A new and unexpected finding is that Fz ligands can stimulate Fz only at high concentrations of Go. At these high concentrations the constitutive activity of hFz1 is inhibited, but the non-constitutive activity can be triggered. This means that the non-constitutive activity of Fz is also restricted to a certain concentration of Go and can be specifically evoked.

On the basis of the non-constitutive activity of Fz or Fz coupled G proteins that is restricted to a certain range G protein concentration the present inventors developed a new assay for measuring the non-constitutive activity of Fz. In this assay the concentrations of G protein to Fz are provided in ratios, wherein the Fz or the Fz coupled G proteins are non-constitutively active. The assay makes use of this well defined restricted concentration range, wherein Fz or Fz coupled G proteins are non-constitutively active. By experimentally presetting the concentration ratios of G protein/Fz to high values the assay defines the kind of activity of Fz that can be triggered by adding ligands. Therefore, the present invention provides an assay for measuring specifically the non-constitutive activity of Fz.

As mentioned above, Fz show the concentration dependent constitutive activity towards G protein. This constitutive activity is sensitive to the concentration of Gαo-GTP molecules released as a result of this constitutive Fz activity, so that the negative feed-back takes place. However, addition of the Fz ligands changes the G protein concentration dependence of the Fz response. At concentrations of Go optimal for constitutive Fz activity, addition of Fz agonists decreases this constitutive Fz activity. In contrast, at high G protein concentrations, when constitutive Fz activity is low, addition of Fz ligand now stimulates Fz activity. This stimulation can also be viewed as a relief of inhibition from high Go concentrations.

In a preferred embodiment of the invention the assay for measuring the non-constitutive activity and the assay for measuring the constitutive activity can be combined consecutively by e.g. changing the provided G protein, Fz or membrane protein concentration.

By the assay of the present invention for measuring the non-constitutive Fz activity the influence of Fz ligands e.g. agonists, antagonists, modulators, effectors etc. as well as all kind of modulators and effectors that are associated with the Fz pathway e.g. effectors that bind to the G protein can be determined. It can be envisioned that e.g. an antagonist of the non-constitutive Fz activity will have an application as a drug reducing Fz activity in e.g. colon cancer or degenerative disorders.

Therefore, both assays of the invention provides a fast and efficient high throughput screening technique to find pharmaceutical modulators of Fz activities that can be preformed by a robot, in a simple, cheap and robust manner with the advantages of a cell free system.

In the most preferred embodiment of the assays of the invention the binding of GTP to G protein is detected as an indicator for Fz receptor activation. A further important advantage of this embodiment over currently used cell transcription based assays is the possibility of identifying substances specifically disrupting interactions of particular Fz ligands with particular Fz, rather than substances acting at a common downstream component of the pathway. Therefore, assays are provided that measure the Fz activity specifically for Fz and/or Fz ligands. Additionally, this direct measurement is not reflecting less or no other interfering down- or upstream interactions.

In a preferred embodiment of the invention the assays for measuring a constitutively or non-constitutively activity of Fz further comprise at least one frizzled receptor ligand Therefore, the assay is provided in a sufficient form.

The assays of the invention can be provided with membrane proteins. In another preferred embodiment the assays of the invention can be provided without membrane proteins and the membrane proteins or Fz and/or Fz ligands can be added afterwards by the user/applicant at the own option and choice of the user/applicant.

Fz receptor ligands can be added as pure extracts, crude preparations, e.g. homogenized samples or lysis samples or conditioned media etc. and/or can be purified after measuring G protein activation. To purify Fz ligands, protein purification techniques as known in the art are applied. For example, several chromatography and filtration steps are performed, whereas eluted fractions are probed for Wnt activity to be collected and applied to further purification.

Outstanding advantages of the assays and methods of the present invention are that they are very fast and simple and can be combined with other assays and methods. For instance, the medium is applied to several chromatography matrixes to purify Wnt ligands from the medium, whereas eluted fractions are probed for Wnt activity to be collected and applied to further purification. Instead of the currently used time-consuming procedures to monitor Wnt activity in these fractions, by application of the assays or methods of the present invention these fractions can be tested for their probability to activate Fz. The fractions inducing higher than constitutive G protein activation are collected and used in subsequent purification steps. Therefore, the assays and methods of the present invention provide the possibility to obtain pure and active Fz ligands in high amounts.

The term "frizzled receptor ligand" as used herein refers to all kinds of ligands binding to frizzled receptors. The term "ligand" refers to a molecule that is able to form a complex with a biomolecule e.g. the Fz, G protein to serve a biological purpose.

In more specific sense, it is an effector molecule binding to a site on a target protein e.g. Fz, G proteins, by intermolecular forces such as ionic bonds, hydrogen bonds, and Van der Waals forces.

In a more preferred embodiment the frizzled receptor ligand is selected from the group consisting of at least one agonist, antagonist, inverse agonist, effector, modulator, natural ligand, artificial ligand, and recombinant ligand.

The term "agonist" as used herein refers to a substance that binds to a specific receptor and triggers a response in the cell. Also included in this definition are partial agonists that also bind and activate receptors, but have only partial efficacy for a receptor compared to a full agonist. They may also be considered as a ligand, which displays both agonistic and antagonistic effects. In the presence of full agonists, partial agonists act as competitive antagonists. Also comprised are co-agonists that cooperate with other co-agonists to produce the desired effect, endogenous, and exogenous agonists. The most prominent Fz agonists are members of the Wnt protein family.

The term "antagonist" as used herein refers to a ligand that block the binding of an agonist at a receptor molecule, inhibiting the signal produced by a receptor-agonist coupling. For example, competitive antagonists reversibly bind to receptors and compete with other agonists and antagonists for a specific binding site. Reversible non-competitive antagonists bind to a different binding-site from the agonists, exerting their action to that receptor via the other binding site. They are called non-competitive antagonists, because they do not compete for the same binding site as the agonists. Irreversible antagonists bind covalently to the receptor binding site. They do not compete with agonists since due to the covalent nature of the bond they can not be displaced from the receptor by raising the concentration of an agonist. Examples of Fz antagonists are Dickkopf, WIF (Wnt inhibiting factor) and sFRP (soluble frizzled related protein).

The term "inverse agonist", also called negative modulator, as used herein refers to an agent, which binds to the same or different receptor binding-site as an agonist for that receptor, but exerts the opposite pharmacological effect. Inverse agonists are effective against certain types of receptors, which have constitutive activity.

The terms "effector", also called "modulator", as used herein refers to molecules that bind to a protein and thereby alters the activity of that protein. A modulator can bind to a regulatory site during allosteric modulation and modulates allosterically the shape of the protein. Apart from allosteric modulators, inhibitors and activators are also included.

The term "natural ligand" as used herein refers to physiological ligands that are naturally occurring. In contrary, the term "artificial ligand" as used herein refers to artificially synthesized ligands e.g. chemically synthesized ligands. Also comprised are modified ligands.

The term "recombinant ligand" as used herein refers to ligands produced by recombination techniques. Recombinant ligands are encoded by recombinant, genetically engineered or modified polynucleotides. Recombinant ligands are cloned in vectors and expressed.

In a further preferred embodiment of the invention the frizzled receptor ligand and/or frizzled receptor is expressed by a vector, preferably in bacteria, most preferably in *Escherichia coli*.

The term "vector" as used herein refers to carriers of foreign, recombinant or modified polynucleotides that are cloned into these vectors for expression, i.e. a vehicle for transferring genetic material into a cell. For instance, vectors are bacterial plasmids, viruses like baculovirus or phages, and yeast vectors. Other examples of preferred bacteria besides *Escherichia coli* are *Shigella flexneri, Salmonella typhimurium, Bacillus subtilis* or *Streptomyces coelicolor*. Fz can be produced in mammalian cells e.g. CHO cells to serve as basis for the in vitro Fz activation assay. It is obvious that there are many more applicable ways to express frizzled receptors, such as production of Fz as inclusion bodies in *E. coli* with subsequent refolding, baculovirus based production in Sf9 cells, expression in various yeast strains, insect cell lines, or many other mammalian cell lines, e.g. HeLa, HEK as well as expression pf Fz in a cell free translation or coupled transcription translation system of bacterial, wheat germ, rabbit reticulocyte, or other origin.

In another embodiment of the invention the system for measuring G protein activity is selected from the group consisting of fluorescent, radioactive and spectrophotometric techniques.

For measuring G protein activity as defined above molecules e.g. GTP or G protein have to be labelled fluorescently, radioactively or spectrophotometrical that their binding can be detected. The radioactive technique depends on radioactive labels that are exposed to X-ray film or measured by scintillation counters. Frequently used radioactive isotopes in these assays are $^{14}C$, $^{32}P$, $^{35}S$ and $^{125}I$. Examples for spectrophotometric detection techniques are fluorescent and colorimetric methods with spectral properties in different ranges of wavelengths. The fluorescent detection technique depends on fluorescent labels like Europium, Oregon Green, Texas Red, or GFP that are excited by proper kinds of light, and the emission of the excitation is then detected by a photosensor, such as CCD camera equipped with appropriate emission filters. The colorimetric detection technique depends on labelling by dyes with different colours that absorb or emit in the range of visible light, whose amount or concentration is measured via densitometry or spectrophotometry. Also comprised are chemiluminescent detection methods that depend on luminescent molecules like enhanced chemiluminescence.

A further aspect concerning the present invention is a method for measuring a constitutive or non-constitutive activity of a frizzled receptor comprising the steps of:

a) providing at least one membrane protein with at least one cell free frizzled receptor;

b) adding at least one frizzled receptor ligand and at least one G protein; and c) incubating the cell free frizzled receptor, the frizzled receptor ligand and the G protein in a system for measuring G protein activity, wherein the detection of guanosine triphosphate (GTP) binding to the G protein indicates the activity of the G protein.

To measure a constitutive or non-constitutive activity of a frizzled receptor at least one cell free frizzled receptor, at least one frizzled receptor ligand and at least one G protein, which have been defined by the above explanations are combined in one tube or well of a plate. In addition, GTP analogue nucleotide such as Europium-GTP, optionally guanosine diphosphate (GDP) and the required buffers and salts are provided. These components were incubated in a system for measuring G protein activation that is selected from the group consisting of fluorescent, radioactive and colorimetric techniques. G proteins can be crude preparations, purified or non-purified extracts from natural sources or artificially produced.

The method for measuring constitutive or non-constitutive activity of Fz is based on the GDP/GTP exchange by activated G proteins. Therefore there is a variety of parameters that can be used directly or indirectly for monitoring the GTP binding to the G protein. For instance, the binding of GTP itself, the uncoupling of GDP by detecting the amount of membrane bound GTP or GDP, respectively, and the amount of free GTP or GDP can be detected.

One system to monitor G protein activation is based on the Europium labelled GTP analogue and time-resolved fluorescence measurements. Other potential systems are e.g. the classical filter-based $^{35}$S-GTPγS assay or the fluorescence enhancement assays using BODIPY-GTPγS molecules that enhance their fluorescence upon binding to G proteins.

In preferred embodiments Fz receptor ligands used for the method of the invention are expressed by a vector preferably in bacteria, most preferably in *Escherichia coli*, and are selected from the group consisting of at least one agonist, antagonist, inverse agonist, effector, modulator, natural, artificial and recombinant ligand as afore mentioned.

A further aspect of the invention concerns a method for obtaining an active non-mammalian frizzled receptor ligand comprising the steps of:
a) performing random and/or directed mutagenesis in at least one polynucleotide sequence encoding at least one inactive frizzled receptor ligand to generate a mutated polynucleotide sequence;
b) digesting the mutated polynucleotide sequence into random polynucleotide fragments;
c) recombining the random polynucleotide fragments to obtain recombinant polynucleotides by at least one recombination technique;
d) cloning the recombinant polynucleotide into a vector;
e) expressing the recombinant polynucleotide resulting in recombined frizzled receptor ligands;
f) measuring the ability of the recombinant frizzled receptor ligands to activate frizzled receptors in a system comprising at least one G protein and at least one membrane protein with at least one frizzled receptor; and
g) repeating step a) to f) until the recombinant frizzled receptor ligands activate the G protein at least 10-fold, preferably 100-fold, more preferably 500-fold, most preferably 1000-fold compared to frizzled receptor ligands encoded by the polynucleotide sequence of step a).

The term "polynucleotide" as used herein refers to chain molecules comprising more than about 10 nucleotides.

The term "active frizzled receptor ligand" as used herein refers to Fz ligands that are able to activate Fz in general. The term "inactive frizzled receptor ligand" as used herein refers to completely inactive and less active Fz ligands that are only able to activate Fz to a low extent.

The term "cloning" as used herein refers to molecular cloning, i.e. a process to create identical copies of polynucleotides. The term "random mutagenesis" as used herein refers to random mutagenesis methods that introduce changes at positions throughout the polynucleotide sequence. In most of these techniques copying of a DNA sequence is deliberately disturbed. These methods include the use of physical and chemical mutagens, mutation strains and some forms of insertion and deletion mutagenesis as well as the various forms of error-prone PCR. Random mutations result from improper polynucleotide replication or inadequate repair of DNA damage. The term "directed mutagenesis" as used herein refers to directed mutagenesis methods that randomize only a specific position within a polynucleotide sequence. These methods involve the direct synthesis of mixtures of DNA molecules and are usually based on the incorporation of partially randomised synthetic DNA cassettes into genes via PCR or direct cloning. The key to these methods is the introduction of diversity at specific positions within the synthetic DNA. The term "recombination technique" as used herein refers to methods, such as DNA shuffling and staggered extension process that take portions of existing sequences and mix them in novel combinations. These methods do not directly create new sequence diversity, but combine existing diversity in new ways. Recombination techniques comprising homologous and non-homologous methods make it possible to bring together advantageous mutations while removing deleterious mutations in a manner analogous to sexual recombination. Methods such as iterative truncation for the construction of hybrid enzymes that make it possible to construct hybrids proteins even when the genes have little or no sequence homology also belong to this category. Directed, random mutagenesis and recombination techniques are summarized by the generic term "protein evolution techniques".

By the method of the present invention for obtaining an active frizzled receptor ligand it is possible to evolve Wnt ligands for efficient production in non-mammalian hosts, ideally *Escherichia coli*. Currently, bacterially-produced Wnt ligands lack biological activity. It is possible to apply protein evolution techniques, such as protein shuffling, to evolve Wnt ligands to a new form with improve biological activity, foldability and stability upon production in bacteria.

The term "non-mammalian frizzled receptor ligand" as used herein refers to Fz ligands that are produced in organisms that are not members of the class mammalian, e.g. in prokaryotic, insect, yeast cells or by viruses. Also comprised are Fz ligands produced by vectors or expression systems.

The principle of the method of the present invention is a combination of a mutagenesis technique e.g. error-prone PCR amplification of the initial sequence with subsequent recombination techniques by digestion into random-size fragments followed by re-assembly, repeated several cycles. In other words, this is a combination of random incorporation of nucleotide changes with recombination. At the end of each cycle, the library of resulting variants of the initial sequence is cloned into a vector, transformed into a host e.g. *Escherichia coli*, expressed, and probed for activity. If the activity of a clone is increased, it is isolated for the next cycle of protein evolution until the activity is multiplied. This technique can be used to improve protein activities tens of thousand times. Therefore, the method of the present invention provides the possibility to obtain pure and active Fz ligands in high amounts.

The existence of an easy and fast assay to monitor Wnt activity is essential for such a method. In a preferred embodiment of the invention the assay for measuring constitutive or non-constitutive activity of Fz of the present invention is used for this purpose.

In a preferred embodiment of the methods according to the invention a concentration of the G protein is approximately 0.4 µg/ml or less, preferably between approximately 0.002 µg/ml and 0.3 µg/ml, more preferably between approximately 0.005 µg/ml and 0.15 µg/ml, most preferably approximately 0.1 µg/ml in relation to approximately 2 µg/ml to 15 µg/ml of the membrane protein.

In another preferred embodiment of the methods according to the invention a concentration of the G protein is approximately 0.3 µg/ml or higher, preferably between approximately 0.035 µg/ml and approximately 10 µg/ml, more preferably approximately 0.4 µg/ml, most preferably approximately 0.5 µg/ml in relation to approximately 2 µg/ml to 15 µg/ml of the membrane protein.

In a preferred embodiment of the invention the frizzled receptor ligand is a Wnt protein. The term "Wnt" as used herein refers to a huge family of signalling molecules of the Fz pathway. These proteins contain a signal sequence of 350-380 amino acids followed by a highly conserved distribution of cysteines. Although Wnt proteins are secreted, they show an insoluble nature that has been explained by the discovery that these proteins are palmitoylated and are more hydrophobic than initially predicted from the primary amino acid sequence. Until now the insolubility of Wnt has impeded methods for purifying Wnt and precluded an isolation of Wnts in high quantities. However, the assays and methods of the present invention overcome this problem and provide the possibility to yield pure and active Wnt in high amounts.

In a preferred embodiment of the invention wherein the step of providing at least one cell free frizzled receptor and/or the step of adding at least one frizzled receptor ligand and at least one G protein is/are preceded by at least one protein evolution technique, as described above.

A further aspect of the invention is the use of the assays of the present invention for screening frizzled receptor ligands and/or for measuring levels of frizzled receptor ligands and/or for measuring levels of frizzled receptors and/or for obtaining active frizzled receptor ligands. The term "levels" as used herein refers to amounts, volumes, concentrations and ratios. Obtaining active Fz ligand in high amounts by a cheap and easy way is great benefit, because ligands can be used e.g. as growth factors, promoting the maintenance and proliferation of stem cells.

A further aspect of the invention is the use of the assays of the present invention, wherein the frizzled receptor ligands are drug candidates, preferably drugs for cancer diseases and degenerative disorders. Evidently, there is a broad variety of diseases that can be treated with pharmaceuticals influencing Fz pathways.

Mis-regulation of the Wnt pathway leads to a variety of abnormalities and degenerative diseases, like tetra-amelia, bone density defects, vascular and retinal defects in the eye, tooth agenesis, colorectal and colon cancer. Mutations that promote constitutive activation of the Wnt signaling pathway lead to cancer. In addition to tooth defects, individuals with Axin2 mutations display for instance a predisposition to colon cancer. Moreover, alterations of Wnts, APC, axin, and TCFs are all associated with carcinogenesis. The best-known example of a disease involving an overactivation of Wnt pathway that produces tumors is familial adenomatous polyposis (FAP), an autosomal, dominantly inherited disease, in which patients display hundreds or thousands of polyps in the colon and rectum. Aberrant activation of the Wnt/Frizzled/beta-catenin signaling pathway leads to tumorigenesis in many tissues. The majority of breast cancers are associated with stabilization of beta-catenin, which is a hallmark of overactivation of this pathway. Specifically, Wnt2, Wnt5a, Wnt7b, Wnt10b, Wnt13/2b, and Wnt14 have been reported as overexpressed in breast cancer as compared to normal breast tissue. Further, most breast cancer cell lines overexpress several Wnt ligands including Wnt3a, Wnt4, Wnt6, Wnt8b, Wnt9a, and Wnt10b. In contrast, expression of the secreted Wnt inhibitors sFRP1 and WIF1 is reduced or lost in most cases of breast cancer. Thus, antagonists of Wnt/Frizzled interactions and molecules inhibiting Fz pathway become immediate anticancer drug candidates. In addition, it gets obvious that Wnt overactivation is a reason for aging and decreased synapse formation. Therefore, inhibitors of Fz pathway can be antidegenerative and memory enhancing drugs.

The embodiments described for the assay of the invention can also be applied to the methods of the invention and vice versa.

DETAILED DESCRIPTION OF THE FIGURES

FIG. 1. Recombinant Human Frizzled Receptor 1 (hFz1) can be Produced in *E. coli* Membranes and can Physically Bind the Heterotrimeric G Protein Go (A) Membrane fractions of control bacteria and bacteria expressing the MBP (maltose binding protein)-hFz1 fusion protein. Two bacterial clones were used, which differ in the level of MBP-hFz1 expression. Western blotting with antibodies to MBP was done. Multiple bands represent different states of the receptor unfolded by sodium dodecyl sulphate (SDS).

(B) hFz1 membranes, but not control bacterial membranes, bind Go. Membranes from (A) were incubated with bovine brain Go heterotrimeric G protein, followed by ultracentrifugation. Amounts of Go in the supernatant (S) and pellet (P) were compared. While control membranes fail to bring Go to the pellet, hFz1 membranes co-precipitate Go. Importantly, hFz1 membranes from clone 2 which express higher levels of hFz1 (see (A)) bind more Go, demonstrating the direct hFz1-Go interactions.

FIG. 2. hFz1 Showed a Basal G Protein-Activating Activity hFz1 was expressed in CHO cells by means of transient transfection. Plasma membranes from these cells, as well as from control non-transfected CHO cells of a similar density, were prepared as described in Materials and Methods. G protein-activating activity of the hFz1 membranes was compared to that of control membranes using the Perkin Elmer Europium-GTP TRF assay at varying amounts of the ectopically added bovine brain Go protein. At proper membrane/Go ratios, hFz1 demonstrates about 3-fold increase of Go protein activation over control membranes.

FIG. 3. Wnt Ligands can Further Stimulate hFz1 Activity Towards Go (A) CHO-produced hFz1 membranes were stimulated with 5 µl Wnt3a-conditioned medium per 100 µl of the reaction volume. *E. coli*-produced hFZ1 membranes were stimulated with 0.3 µg/ml purified Wnt3a. For comparison, CHO membranes expressing human fMLP receptor hFRP1 as an example of an unrelated known GPCR from Perkin Elmer were stimulated to a similar extent with 1 µM formyl-peptide ligand.

(B) *E. coli* produced hFz1 membranes can be stimulated with the Wnt5a mimetic peptide fMDGCEL (Safholm A. et al, 2006).

FIG. 4. Detergent-Solubilized hFz1 Stimulated GTP Incorporation into Go in the Presence of Different Wnt Ligands Addition of Wnt5a, Wnt5b, Wnt7a induced concentration-dependent activation of the trimeric Go protein in the presence of hFz1-expressing membrane fractions, but not control membranes. Among the Wnt ligands tested, Wnt3a and Wnt5a were most active, while Wnt5b and Wnt7a demonstrated a more modest stimulation (FIG. 4). Statistical significance is shown as "*", "", and "*" (P value by unpaired t-test<0.05, <0.005, and <0.001, respectively).

FIG. 5. Wnt Ligands Stimulate Several Frizzled Receptors to Activate the Trimeric G Proteins To demonstrate that other Frizzled receptors than hFz1 can be investigated by the in vitro G protein activation assay according to the invention, human Frizzled receptors 6 and 7 (hFz6, hFz7) were bacterially expressed. When tested for their ability to activate Go upon addition of different ligands, hFz6 activated Go in the presence of Wnt7a and to a lesser extent Wnt5a (FIG. 5A), while hFz7 was mostly stimulated by Wnt5a (FIG. 5B). The results obtained with three human Frizzled receptors (hFz1, hFz6, hFz7) and four Wnt ligands (Wnt3a, Wnt5a, Wnt5b, and Wnt7a) allow to compose a table of pair-wise Wnt-Frizzled activations using Go stimulation as the read-out (FIG. 5C).

Detergent-solubilized hFz6 and Fz7 stimulated GTP incorporation into Go in the presence of different Wnt ligands. Data are presented in FIG. 5C as summary of the capacity of the tested Wnt ligands to stimulate the tested Frizzled receptors to activate Go in vitro. Control membranes showed no Go activation in the presence of any Wnt. Go activation by the Wnt-Frizzled pairs is denoted (in the order of the decreasing activation capacity) as "+++", "++", "+", "+/−", and "−" using as criteria the lowest Go-activating Wnt concentration as well as the maximal Go activation level achieved by any Wnt concentration.

Materials and Methods

1. HFz1 Expression in Bacteria

The coding sequence of hFz1 was cloned in-frame into the pMAL-p2 plasmid (New England BioLabs) allowing expression of the protein as an N-terminal fusion with maltose binding protein (MBP). The natural signal sequence of MBP directs the fusion protein through the cytoplasmic membrane. Expression conditions were optimized to allow slow expression to maximize correct hFz1 folding: Expression was performed at 18° C. for 18 h, and in the presence of glucose to minimize the expression of endogenous MBP protein.

Bacteria were harvested by centrifugation, resuspended in PBS (phosphate-buffered saline) and disrupted by French press. The resultant suspension was cleared from the cell debris by low-speed centrifugation, followed by ultracentrifugation to pellet the membranes expressing MBP-hFz1. The membranes were resuspended in PBS supplemented with the protease-inhibitor cocktail (Roche) and frozen in aliquots at −80° C. Control bacteria were transformed with the empty pMAL-p2 vector, induced with IPTG, grown and harvested in parallel with hFz1-transformed bacteria.

2. HFz1 Expression in CHO (Chinese Hamster Ovary) Cells.

HFz1 coding sequence was subcloned into pIRES2-DsRed-Express plasmid (Invitrogen). CHO cells were transiently transfected with lipofectamine following manufacturer's protocol. Transfection efficiency was estimated to be >50%. Two days post-transfection, transfected cells in parallel with control non-transfected cells of a similar cell density were washed, detached with EDTA, pelleted, washed with PBS, and disrupted in a glass-rod homogenizer in a hypotonic buffer (10 mM Hepes pH 7.5). Membrane fraction was prepared and stored as above.

3. Europium-GTP Assay of G Protein Activation

Europium-GTP assay of G protein activation using a time-resolved fluorescence assay was performed. In one well of a 96-well AcroWell plate, 100 µl were mixed containing 4-10 µg/ml membrane protein from the hFz1 expression in bacteria or in CHO, 50 mM Hepes, pH 7.4, 1 mM $MgCl_2$, 50 mM NaCl and 1 mg/ml saponin. Bacterial membranes expressing hFz1 or bacterial control membranes were used at 0.1 mg/ml protein concentration for membrane protein preparation. CHO membranes expressing hFz1 or CHO control membranes were used at 0.01 mg/ml protein concentration. Varying amounts of the following were added: bovine brain Go (Calbiochem), Wnt3a (R&Dsystems), Wnt3a-conditioned or control L-cell medium. Extra GDP was omitted in most experiments. 30 min after incubating this mixture at room temperature on a shaker (100 rpm), Europium-GTP was added, and incubation was continued for 30 more min. Afterwards the content of the wells was filtered and washed using the Multiscreen Vacuum Manifold (Millipore). Amounts of Europium-GTP retained by the membranes were then measured using the Perkin Elmer Victor3 Multilabel Plate Reader.

4. DNA Shuffling as a Directed Protein Evolution Technique

Point mutations are induced by error-prone PCR into wnt genes generating a library of Wnt coding DNA with randomized point mutations. Therefore, $Mn^{2+}$ or $Mg^{2+}$ is added to a standard PCR reaction mixture with wnt genes to impose imperfect reaction conditions.

This library was the substrate for the subsequent DNA shuffling reaction. For DNA shuffling, mutated DNA is digested into random fragments with DNase I. Fragments are resuspended in a standard PCR mix with different synthetic chimeric oligonucleotides for amplification, wherein the fragments are spliced together randomly. The spliced wnt gene fragments are then assembled by primerless PCR. Individual fragments prime against each other to recreate a full-length recombinant wnt gene. Diversity in this DNA shuffling was controlled by the number of different mutated wnt genes recombinant. The resulting new gene library is cloned into bacterial vector pMAL-p2, transformed and expressed for testing the ability of Wnt to activate G protein.

5. Wnt Protein Purification

To purify Wnt protein as an example for a typical Fz ligand LWnt3A or LWnt5A cell lines producing and secreting Wnt proteins were used. By growing the cells adherent for 4 days from a 1:10 to 1:20 split high amounts of Wnt-3A were obtained. The medium was DMEM plus 10% FBS, omitting the serum lowers the levels of Wnt protein in the medium. The Wnt containing medium was filtered, detergent was added (Triton X-100 or CHAPS) to a final concentration of 1%, and the medium was refiltered just before applying the material to Blue Sepharose.

Purification by Blue Sepharose fractionation yielded pure Wnt protein, wherein Wnt3A conditioned medium was applied on a Blue Sepharose HP column. Wnt elution from Blue Sepharose was done in a single step from 150 mM to 1.5 M KCl. Approximately, half of the Wnt protein eluted immediately with the salt and the majority of contaminants, but the other half was retained and eluted later in a second pool. This second pool contained much less total protein and consequently contained a higher proportion of Wnt.

Pooled eluted Wnt fractions from Blue Sepharose purification were concentrated by gel filtration to 5 or 10 ml volume using Centricon or Amicon Ultra 30 ultrafiltration device (Amicon) depending on size of gel filtration column.

A heparin cation exchange chromatography served the purpose of further concentrating the protein and removing predominant contaminants as most likely BSA. The final concentration of Wnt3A was about 0.1 mg/ml. If the concentration is higher, a precipitate will form which is predominately Wnt protein. This precipitate can be pelleted easily. The remaining supernatant contains Wnt3A at about 0.1 mg/ml while the pellet contains largely inactive Wnt protein. Therefore, the present conditions (1×PBS, 1M NaCl, 1% CHAPS, pH7.3) could maintain the solubility and activity of Wnt3A at a maximum of 0.1 mg/ml.

All purification steps were carried out at 4° C., and purified protein was also stored at 4° C. Protein can also be freeze-dried with retention of activity.

REFERENCES

Borchert K. et al., Assay and Drug Development Technologies, 3(2), 133-141, 2005.
Brennan K. and Brown M., Journal of Mammary Gland Biology and Neoplasia, 9(2), 119-131, 2004.
DasGupta R. et al., Science 308, 826, 2005.
Huang H. and Klein P., Genome Biology, 5 (234), 1-7, 2004.
Le Garrec J. et al., Developmental Dynamics, 235, 235-46, 2006
Logan C. and Nusse R., Annu. Rev. Cell Dev. Biol., 20,781-810, 2004.
Säfholm A. et al., J. Biol. Chem., 281(5), 2740-9, 2006.
Willert K. et al., Nature 423, 448-452, 2003.

The invention claimed is:

1. A cell-free assay product for measuring a constitutive activity of frizzled receptors comprising at least one G protein, at least one system for measuring G protein activity and at least one membrane protein with at least one frizzled receptor, wherein a concentration of the G protein is approximately 0.4 µg/ml or less.

2. The product of claim 1, wherein a concentration of the G protein is between approximately 0.002 µg/ml and 0.3 µg/ml.

3. The product of claim 2, wherein a concentration of the G protein is between approximately 0.005 µg/ml and 0.15 µg/ml.

4. The product of claim 3, wherein a concentration of the G protein is approximately 0.1 µg/ml in relation to approximately 4 µg/ml to 10 µg/ml of the membrane protein.

5. The assay product of claim 1 wherein the system for measuring G protein activity is selected from the group consisting of fluorescent, radioactive and spectrophotometric techniques.

6. The assay product of claim 1 further comprising at least one frizzled receptor ligand.

7. The assay product of claim 6, wherein the frizzled receptor ligand is at least one modulator of frizzled receptor activity.

8. The assay product of claim 6, wherein the frizzled receptor ligand is at least one antagonist.

9. The assay product of claim 6, wherein the frizzled receptor ligand is at least one agonist, comprising inverse agonists.

10. The assay product of claim 6, wherein the frizzled receptor ligand is at least one natural ligand.

11. The assay product of claim 6, wherein the frizzled receptor ligand is at least one artificial ligand, comprising recombinant ligands.

12. The assay product of claim 6 wherein the frizzled receptor ligand and/or frizzled receptor is/are expressed by a vector.

13. The product of claim 12, wherein the vector is expressed in bacteria or in *Escherichia coli*.

14. A cell-free assay product for measuring a non-constitutive activity of frizzled receptors comprising a G protein, at least one system for measuring G protein activity and at least one membrane protein with at least one frizzled receptor, wherein a concentration of the G protein is approximately 0.3 µg/ml or higher.

15. The product of claim 14, wherein a concentration of the G protein is between approximately 0.035 µg/ml and 10 µg/ml.

16. The product of claim 15, wherein a concentration of the G protein is approximately 0.4 µg/ml.

17. The product of claim 16, wherein a concentration of the G protein is approximately 0.5 µg/ml in relation to approximately 4 µg/ml to 10 µg/ml of the membrane protein.

18. A method comprising screening frizzled receptor ligands, measuring levels of frizzled receptor ligands, measuring levels of frizzled receptors, or obtaining active frizzled receptor ligands using the assay product of claim 1.

* * * * *